United States Patent
Bresler et al.

(10) Patent No.: US 10,427,993 B2
(45) Date of Patent: Oct. 1, 2019

(54) PROCESS FOR RECOVERING BENZENE AND FUEL GAS IN AN AROMATICS COMPLEX

(71) Applicant: UOP LLC, Des Plaines, IL (US)

(72) Inventors: Leonid Bresler, Northbrook, IL (US); Patrick C. Whitchurch, Sleepy Hollow, IL (US); Jason T. Corradi, Arlington Heights, IL (US)

(73) Assignee: UOP LLC, Des Plaines, IL (US)

( * ) Notice: Subject to any disclaimer, the term of this patent is extended or adjusted under 35 U.S.C. 154(b) by 46 days.

(21) Appl. No.: 15/692,210

(22) Filed: Aug. 31, 2017

(65) Prior Publication Data

US 2019/0062237 A1      Feb. 28, 2019

(51) Int. Cl.
| | | |
|---|---|---|
| *C07C 7/04* | (2006.01) | |
| *C07C 7/00* | (2006.01) | |
| *C07C 15/04* | (2006.01) | |
| *C07C 15/08* | (2006.01) | |
| *C07C 5/27* | (2006.01) | |
| *C07C 7/09* | (2006.01) | |
| *C07C 7/10* | (2006.01) | |

(52) U.S. Cl.
CPC .............. *C07C 7/04* (2013.01); *C07C 5/2702* (2013.01); *C07C 7/005* (2013.01); *C07C 7/09* (2013.01); *C07C 7/10* (2013.01); *C07C 15/04* (2013.01); *C07C 15/08* (2013.01)

(58) Field of Classification Search
CPC .. C07C 7/00; C07C 7/04; C07C 15/04; C07C 15/08
See application file for complete search history.

(56) References Cited

U.S. PATENT DOCUMENTS

| | | | |
|---|---|---|---|
| 4,113,787 A | * | 9/1978 | Ward .................. C07C 5/32 585/441 |
| 4,842,836 A | | 6/1989 | Lok et al. |
| 4,910,006 A | | 3/1990 | Zones et al. |
| 4,963,337 A | | 10/1990 | Zones |
| 4,965,233 A | | 10/1990 | Speronello |
| 5,043,502 A | | 8/1991 | Martindale et al. |
| 5,512,267 A | | 4/1996 | Davis |
| 5,900,523 A | | 5/1999 | Kulprathipanja |

(Continued)

FOREIGN PATENT DOCUMENTS

| | | |
|---|---|---|
| CN | 102372585 A | 3/2012 |
| CN | 102372586 B | 3/2014 |

(Continued)

OTHER PUBLICATIONS

Tan et. al., Para-selective methylation of toluene with methanol over nano-sized ZSM-5 catalysts: Synergistic effects pf surface modifications with SiO2, P2O5and MgO, Microporous and Mesoporous Materials, v 196, p. 18-30, Sep. 15, 2014.

(Continued)

*Primary Examiner* — Brian A McCaig

(57) ABSTRACT

A process for separating xylene from a feedstock in which the feedstock is separated into a xylene stream, a benzene rich stream and a light ends stream. Two separation zones may be utilized in which liquid from both is sent to a compression zone and the vapor from the compression zone is combined with a stream prior to the stream entering the second separation zone.

17 Claims, 1 Drawing Sheet

(56) References Cited

U.S. PATENT DOCUMENTS

| | | | |
|---|---|---|---|
| 6,049,018 | A | 4/2000 | Calabro |
| 6,616,899 | B1 | 9/2003 | Upson |
| 6,706,938 | B2 | 3/2004 | Roeseler et al. |
| 6,869,521 | B2 | 3/2005 | Lomas |
| 8,993,825 | B2 | 3/2015 | Werba et al. |
| 9,295,970 | B1 | 3/2016 | Tinger et al. |
| 9,302,955 | B2 | 4/2016 | Corradi et al. |
| 9,309,169 | B2 | 4/2016 | Ou et al. |
| 9,469,579 | B2 | 10/2016 | Molinier et al. |
| 9,527,007 | B2 | 12/2016 | Whitchurch et al. |
| 9,908,061 | B2 | 3/2018 | Dunet et al. |
| 2003/0092952 | A1 | 5/2003 | Netzer |
| 2005/0167338 | A1 | 8/2005 | Miller et al. |
| 2009/0318696 | A1 | 12/2009 | Strohmaier et al. |
| 2012/0149958 | A1 | 6/2012 | Ellrich et al. |
| 2014/0100398 | A1 | 4/2014 | Jin et al. |
| 2015/0246858 | A1 | 9/2015 | Corradi et al. |
| 2017/0073285 | A1 | 3/2017 | Whitchurch et al. |
| 2017/0137350 | A1 | 5/2017 | Weiss et al. |

FOREIGN PATENT DOCUMENTS

| | | | |
|---|---|---|---|
| CN | 104418698 | B | 8/2016 |
| CN | 105837389 | | 8/2016 |
| JP | 57032233 | A | 2/1982 |
| KR | 1317565 | B1 | 10/2013 |
| TW | 201434796 | A | 9/2014 |
| WO | 2016094752 | A2 | 6/2016 |

OTHER PUBLICATIONS

Li et. al., Reaction Mechanism of Toluene Methylation with Dimethyl Carbonate or Methanol Catalyzed by H-ZSM-5, Acta Physico-Chimica Sinica, v 29, n. 7, p. 1467-78, Jul. 2013.

Lu et. al., Effects of controlled SiO2 deposition and phosphorus and nickel doping on surface acidity and diffusivity of medium and small sized HZSM-5 for para-selective alkylation of toluene by methanol, Applied Catalysis A: General, v 453, p. 302-309, Feb. 26, 2013.

Lobo et. al., CIT-1: A New Molecular Sieve with Intersecting Pores Bounded by 10- and 12-Rings, J. Am. Chem. Soc. 1995, 117, 3766-79.

Broughton, "The Parex Process for Recovering Paraxylene", Chemical Engineering Progress, vol. 66, No. 9, p. 70.

U.S. Appl. No. 15/692,480, filed Aug. 31, 2017.
U.S. Appl. No. 15/691,037, filed Aug. 31, 2017.
U.S. Appl. No. 15/692,555, filed Aug. 31, 2017.
U.S. Appl. No. 15/691,104, filed Aug. 31, 2017.

International Search Report from corresponding PCT application No. PCT/US2018/047576, dated Nov. 29, 2018.

Written Opinion of the International Search Authority for corresponding PCT application No. PCT/US2018/047576, dated Nov. 29, 2018.

Search report from corresponding Taiwanese application No. 107121045, dated May 2, 2019.

\* cited by examiner

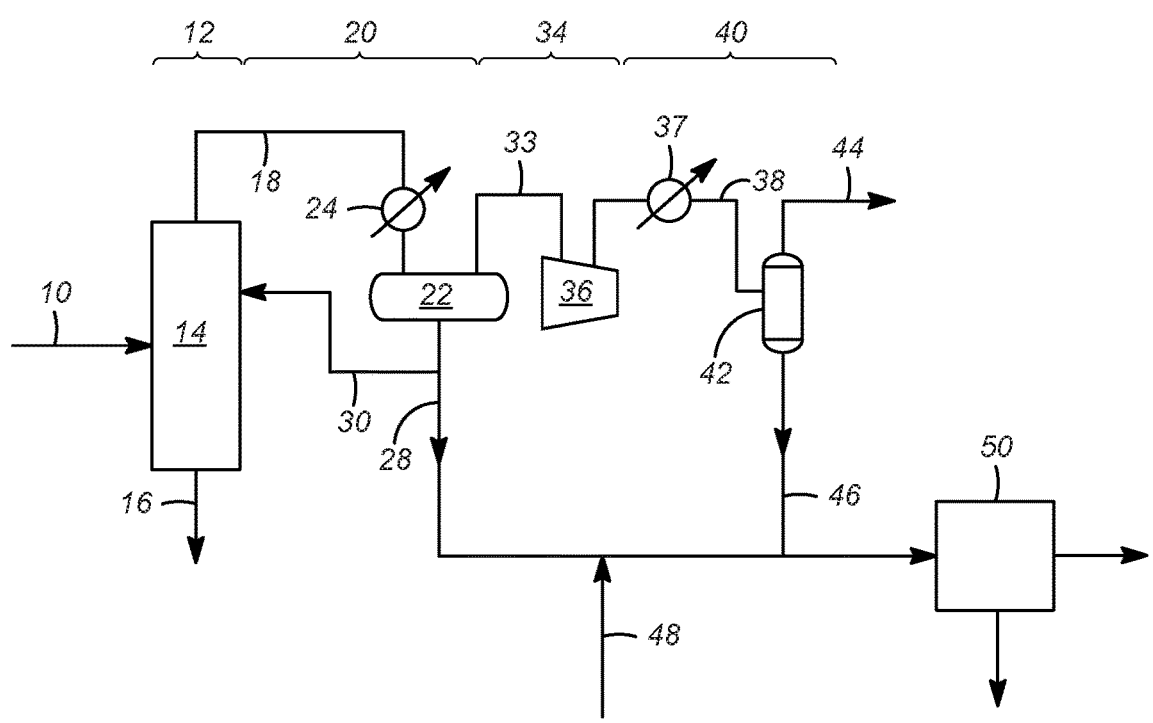

PROCESS FOR RECOVERING BENZENE AND FUEL GAS IN AN AROMATICS COMPLEX

FIELD

This invention relates to an improved process for energy savings in the distillation of hydrocarbons. More specifically, the present invention concerns energy conservation within an aromatics-processing complex producing xylene isomers, benzene and fuel gas.

BACKGROUND

The xylene isomers are produced in large volumes from petroleum as feedstocks for a variety of important industrial chemicals. The most important of the xylene isomers is para-xylene, the principal feedstock for polyester, which continues to enjoy a high growth rate from large base demand. Ortho-xylene is used to produce phthalic anhydride, which supplies high-volume but relatively mature markets. Meta-xylene is used in lesser, but growing, volumes for products such as plasticizers, azo dyes and wood preservers. Ethylbenzene generally is present in xylene mixtures and is occasionally recovered for styrene production, but is usually considered a less-desirable component of C8 aromatics.

Among the aromatic hydrocarbons, the overall importance of xylenes rivals that of benzene as a feedstock for industrial chemicals. Xylenes and benzene are produced from petroleum by reforming naphtha, but not in sufficient volume to meet demand; thus, conversion of other hydrocarbons is necessary to increase the yield of xylenes and benzene. Often toluene is de-alkylated to produce benzene or selectively disproportionated to yield benzene and C8 aromatics from which the individual xylene isomers are recovered.

Aromatics complexes producing xylenes are substantial consumers of energy, notably in distillation operations to prepare feedstocks and separate products from conversion processes. The separation of xylenes from a feedstock in particular offers substantial potential for energy savings. Energy conservation in such processes would not only reduce processing costs, but also address current concerns about carbon emissions.

In addition to producing xylenes, valuable fuel gas is generated during the catalytic conversion of xylenes in an aromatics complex. A portion of this fuel gas is recoverable in a xylene isomerization unit.

The xylene isomerization units typically include a deheptanizer and a stabilizer. The current designs for xylene isomerization units utilize at least two recycle loops between the deheptanizer and the stabilizer.

In the first recycle loop, at least a portion of the overhead vapor from the stabilizer is recycled back to the deheptanizer. This will result in this portion of the vapor being re-condensed, re-flashed, and ultimately re-compressed in the same separation process since it is passed back to the deheptanizer and will pass through the same separation equipment.

The second recycle loop is formed between a receiver and a vent drum where the chilled liquid from the vent drum enters the hotter, low pressure receiver and re-flashes into vapor to the compressor. This requires the same compounds to be re-compressed and cooled once again.

It is believed that the current design is inefficient at least because both of the recycle loops lead to undesirable re-processing of the same material at the expense of equipment capacity and utility cost. Energy conservation in such processes would not only reduce processing costs but also would address current concerns about carbon emissions.

Therefore, there is a need to provide a xylene isomerization process which may be carried out more efficiently.

SUMMARY

The present disclosure describes a process related to an improved process for energy savings in the distillation of hydrocarbons. This disclosure eliminates the need for a stabilization zone, allowing the first liquid stream, which is mostly toluene, can be sent to a toluene recovery zone. This eliminates the need for costly extraction.

In the foregoing, all temperatures are set forth in degrees Celsius and, all parts and percentages are by weight, unless otherwise indicated. Other objects, advantages and applications of the present invention will become apparent to those skilled in the art from the following detailed description and drawing. Additional objects, advantages and novel features of the examples will be set forth in part in the description which follows, and in part will become apparent to those skilled in the art upon examination of the following description and the accompanying drawing or may be learned by production or operation of the examples. The objects and advantages of the concepts may be realized and attained by means of the methodologies, instrumentalities and combinations particularly pointed out in the appended claims.

BRIEF DESCRIPTION OF THE DRAWING

The FIGURE is simplified process flow diagram in which the FIGURE shows a xylene isomerate recovery process according to one or more embodiments of the present invention.

DETAILED DESCRIPTION

The following detailed description is merely exemplary in nature and is not intended to limit the application and uses of the embodiment described. Furthermore, there is no intention to be bound by any theory presented in the preceding background or the following detailed description.

The description of the apparatus of this invention is presented with reference to the attached FIGURE. The FIG. 1s a simplified diagram of the preferred embodiment of this invention and is not intended as an undue limitation on the generally broad scope of the description provided herein and the appended claims. Certain hardware such as valves, pumps, compressors, heat exchangers, instrumentation and controls, have been omitted as not essential to a clear understanding of the invention. The use and application of this hardware is well within the skill of the art.

A process has been developed for separating xylene from a feedstock. The feedstock to the present process generally comprises alkylaromatic hydrocarbons of the general formula $C_6H_{(6-n)}R_n$, where n is an integer from 0 to 5 and each R may be $CH_3$, $C_2H_5$, $C_3H_7$, or $C_4H_9$, in any combination. The aromatics-rich feedstock to the process of the invention may be derived from a variety of sources, including without limitation catalytic reforming, steam pyrolysis of naphtha, distillates or other hydrocarbons to yield light olefins and heavier aromatics-rich byproducts (including gasoline-range material often referred to as "pygas"), and catalytic or thermal cracking of distillates and heavy oils to yield products in the gasoline range. Products from pyrolysis or other cracking operations generally will be hydrotreated according to processes well known in the industry before being charged to the complex in order to remove sulfur, olefins and other compounds which would affect product quality and/or damage catalysts or adsorbents employed therein. Light cycle oil from catalytic cracking also may be beneficially hydrotreated and/or hydrocracked according to known technology to yield products in the gasoline range; the hydrotreating preferably also includes catalytic reforming to yield the aromatics-rich feed stream. If the feedstock is catalytic reformate, the reformer preferably is operated at high severity to achieve high aromatics yield with a low concentration of nonaromatics in the product.

The FIGURE shows a simplified flow diagram of a xylene isomerate recovery portion of an aromatics-processing complex for a feedstock which typically contains olefinic compounds and light ends, e.g., butanes and lighter hydrocarbons and such as pentanes, as well as benzene, toluene and C8 aromatics and higher aromatics and aliphatic hydrocarbons including naphthenes.

The feedstock is introduced via a line 10 to a xylene separation zone 12. The xylene separation zone 12 includes a column 14. Preferably the column 14 is a distillation column, and most preferably a deheptanizer. As will be appreciated by one of ordinary skill in the art, such a column 14 may contain trays or mechanical packing.

In the xylene separation zone 12, the feedstock is separated into a vapor phase and a liquid phase. The liquid phase contains most of the xylene as well as other heavier hydrocarbons. The liquid phase may be recovered from the xylene separation zone 12 via a line 16 and passed to further processing units to recover the desired xylene isomer and other valuable byproducts. The further processing units are known to those of ordinary skill in the art and are not necessary for a full understanding of the present invention.

The vapor phase in the xylene separation zone 12 contains hydrocarbons with seven carbon atoms or less, benzene, and toluene. As will be appreciated by those of ordinary skill in the art, when separating hydrocarbons, there are equilibrium distributions of components in vapor and liquid streams in close contact during the separation processes and thus, the present invention is intended to accommodate a range of aromatic and non-aromatic component purities.

The vapor phase is recovered from the xylene separation zone 12 and passed via a line 18 to a first separation zone 20. Within first separation zone 20, the vapor phase is partially condensed. Accordingly, a condenser 24 is provided in the line 18 used to pass the vapor phase from the xylene separation zone 12 to the first separation zone 20.

The first separation zone 20 typically includes a vessel 22. Preferably the vessel 22 of the first separation zone 20 has a temperature between approximately 32° C. to 149° C. In the vessel 22, the mixed vapor and liquid phases from condenser 24 are separated into a first liquid phase and a first vapor phase. The first liquid phase comprises benzene and toluene as well as soluble levels of hydrocarbons with five carbons or less dissolved into the liquid phase. The first vapor phase comprises mostly hydrogen, and hydrocarbons with four carbons or less. Again, there will be some crossover amounts of compounds. A portion of the first liquid phase from the first separation zone 20 may be recycled to the xylene separation zone 12 via a line 30, and the toluene rich liquid phase is sent to a toluene recovery zone via line 28.

The first vapor phase from the first separation zone 20 is passed via a line 33 to a compression zone 34 in which the first vapor phase is compressed into a compressed vapor phase. The compression zone 34 includes at least a compressor 36. Preferably, the first vapor phase is cooled and partially condensed in the compression zone 34 as well. Accordingly, the compression zone 34 includes a condenser 37.

From the compression zone 34, the compressed and partially condensed first vapor phase is passed via a line 38 to a second separation zone 40 which typically includes a vessel 42 typically having an inlet distributor to facilitate the separation of the compressed vapor phase, and which may also have a drop leg for decanting a heavy aqueous liquid phase that can be formed if water is present in the column feed or may otherwise enter the column overhead system. The temperature of the second separating zone 40 is typically between approximately 10° C. to 149° C. In the second separation zone 40, the compressed and partially condensed first vapor phase is separated into a second liquid phase and a second vapor phase.

The second vapor phase comprises a light ends vapor stream which includes hydrocarbons having four carbon atoms or less and hydrogen. The light ends vapor stream may be recovered from the second separation zone 40 via a line 44, and, for example, may be passed back to a reaction zone (not shown), may be used as fuel, or be used for other processes.

The present invention is shown in the FIGURE avoids wasted energy caused by unnecessary re-extraction of toluene. The benzene in the first vapor phase from the first separation zone 20 and the benzene co-boiling species are concentrated and sent directly to extraction zone 50 via line 46 from the second separation zone 40 while the toluene-rich first liquid phase is sent to a toluene recovery zone via line 28.

In the first separation zone 20, the first liquid phase contains mostly toluene. To avoid an energy penalty associated with re-extraction of toluene, the first liquid phase is directed to a toluene recovery zone instead of the stabilization zone. A portion of the first liquid phase from the first separation zone 20 may be recycled to the xylene separation zone 12 via a line 30. The toluene recovery zone may be realized in a Stripper column commonly found a transalkylation unit thereby effecting a degree of stabilization of the first liquid phase as well. Vapor from the first separation zone 20 is sent to the compression zone 34. Compression zone 34 includes condenser 37 and the compressed and partially condensed vapor phase is directed to a second separation zone 40 via a line 38.

In the present invention the second separation zone 40 includes only a vessel 42 to separate the compressed and partially condensed vapor phase into a second vapor phase product removed via line 44 and a benzene rich second liquid phase removed via line 46. The benzene-rich second liquid phase may also be combined with another benzene rich stream from, for example, an aromatic transalkylation unit via a line 48. In the prior art, the combined liquid is sent to a stabilization zone. However, in the present invention, there is no stabilization zone. In the present invention the combined liquid stream from lines 46, 48 is sent to extraction zone 50. Unlike the prior art, the first liquid stream, which is mostly toluene, doesn't have to be sent to a stabilization zone, where liquid goes on to costly extraction.

As will be appreciated, a process according to one or more of these embodiments provides an effective and efficient process to separate xylene from a reaction effluent. More specifically, in one or more embodiments of the present invention, stabilization zone is eliminated such that the second liquid phase is sent directly to extraction. Unnecessary re-compression of overhead vapor from the stabilization zone is eliminated.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims and their legal equivalents.

While the invention has been described with what are presently considered the preferred embodiments, it is to be understood that the invention is not limited to the disclosed embodiments, but it is intended to cover various modifications and equivalent arrangements included within the scope of the appended claims.

SPECIFIC EMBODIMENTS

While the following is described in conjunction with specific embodiments, it will be understood that this description is intended to illustrate and not limit the scope of the preceding description and the appended claims.

A first embodiment of the invention is a process for the recovery of a benzene rich liquid stream and a light ends vapor stream in a xylene isomerization process from a feedstock, the process comprising passing a feedstock into a deheptanizer in which the feedstock is separated into a deheptanizer vapor phase and a deheptanizer liquid phase, the deheptanizer vapor phase containing hydrocarbons with seven carbon atoms or less, and the deheptanizer liquid phase containing hydrocarbons with eight carbon atoms or more; passing the deheptanizer vapor phase from the deheptanizer to a first separation zone; separating the deheptanizer vapor phase in the first separation zone into a first liquid phase and a first vapor phase; passing the first liquid phase from the first separation zone to a toluene recovery zone; passing the first vapor phase from the first separation zone to a compression zone in which the first vapor phase is compressed and partially condensed to provide a compressed and partially condensed vapor phase; passing the compressed and partially condensed vapor phase from the compression zone to a second separation zone; separating the compressed and partially condensed vapor phase into a second liquid phase and a second vapor phase in the second separation zone, the second vapor phase being a light ends vapor stream; recovering the light ends vapor stream; passing the second liquid phase to an extraction zone; and sending the benzene rich liquid stream to the extraction zone. An embodiment of the invention is one, any or all of prior embodiments in this paragraph up through the first embodiment in this paragraph further comprising passing a portion of the first liquid phase to the deheptanizer. An embodiment of the invention is one, any or all of prior embodiments in this paragraph up through the first embodiment in this paragraph further comprising passing the benzene rich liquid stream to an extraction zone to recover a benzene stream. An embodiment of the invention is one, any or all of prior embodiments in this paragraph up through the first embodiment in this paragraph further comprising passing the benzene rich liquid stream to storage. An embodiment of the invention is one, any or all of prior embodiments in this paragraph up through the first embodiment in this paragraph further comprising compressing the deheptanizer vapor stream before the deheptanizer vapor stream enters the first separation zone. An embodiment of the invention is one, any or all of prior embodiments in this paragraph up through the first embodiment in this paragraph wherein a temperature of the first separation zone is between approximately 32° C. to 149° C. An embodiment of the invention is one, any or all of prior embodiments in this paragraph up through the first embodiment in this paragraph wherein a temperature of the second separation zone is between approximately 10° C. to 149° C. An embodiment of the invention is one, any or all of prior embodiments in this paragraph up through the first embodiment in this paragraph wherein a temperature of the first separation zone is between approximately 10° C. to 149° C. and a temperature of the second separation zone is between approximately 10° C. to 149° C.

A second embodiment of the invention is a process for the recovery of a benzene rich liquid stream and a light ends vapor stream in a xylene isomerization process from a feedstock, the process comprising passing a feedstock into a distillation column in which the feedstock is separated into a distillation vapor and a distillation liquid, the distillation vapor containing mostly hydrocarbons with seven carbon atoms or less; condensing the distillation vapor; separating the distillation vapor into a first liquid phase and a first vapor phase; passing the first liquid phase to a toluene recovery zone; compressing the first vapor phase into a compressed vapor phase; separating the compressed vapor phase into a second liquid phase and a second vapor phase, the second vapor phase being a light ends vapor stream; recovering the light ends vapor stream; passing the second liquid phase to an extraction zone; and recovering and sending the benzene rich liquid stream to an extraction zone. An embodiment of the invention is one, any or all of prior embodiments in this paragraph up through the second embodiment in this paragraph wherein a temperature of the first liquid phase is between approximately 32° C. to 149° C. An embodiment of the invention is one, any or all of prior embodiments in this paragraph up through the second embodiment in this paragraph wherein a temperature of the compressed vapor phase is between approximately 10° C. to 149° C. An embodiment of the invention is one, any or all of prior embodiments in this paragraph up through the second embodiment in this paragraph further comprising passing a portion of the first liquid phase to the distillation column. An embodiment of the invention is one, any or all of prior embodiments in this paragraph up through the second embodiment in this paragraph further comprising passing the benzene rich liquid stream to an extraction zone to recover a benzene stream. An embodiment of the invention is one, any or all of prior embodiments in this paragraph up through the second embodiment in this paragraph further comprising passing the benzene rich liquid stream to storage.

A third embodiment of the invention is a process for the recovery of a benzene rich liquid stream and a light ends vapor stream in a xylene isomerization process from a feedstock, the process comprising passing a feedstock into a separation zone in which the feedstock is separated into a vapor stream and a liquid stream, the vapor stream containing mostly hydrocarbons with seven carbon atoms or less, the liquid stream comprising xylene; condensing the vapor stream; separating the vapor stream into a first liquid phase and a first vapor phase; passing the first vapor phase to a compression zone; compressing the first vapor phase into a compressed vapor phase; separating the compressed vapor phase into a second liquid phase and a second vapor phase, the second vapor phase being a light ends vapor stream; recovering the light ends vapor stream; passing the second liquid phase to an extraction zone; and recovering and sending the benzene rich liquid stream to the extraction zone. An embodiment of the invention is one, any or all of prior embodiments in this paragraph up through the third embodiment in this paragraph wherein a temperature of the first liquid phase is between approximately 32° C. to 149° C. An embodiment of the invention is one, any or all of prior embodiments in this paragraph up through the third embodiment in this paragraph wherein a temperature of the compressed vapor phase is between approximately 10° C. to 149° C.

Without further elaboration, it is believed that using the preceding description that one skilled in the art can utilize the present invention to its fullest extent and easily ascertain the essential characteristics of this invention, without departing from the spirit and scope thereof, to make various changes and modifications of the invention and to adapt it to various usages and conditions. The preceding preferred specific embodiments are, therefore, to be construed as merely illustrative, and not limiting the remainder of the disclosure in any way whatsoever, and that it is intended to cover various modifications and equivalent arrangements included within the scope of the appended claims.

In the foregoing, all temperatures are set forth in degrees Celsius and, all parts and percentages are by weight, unless otherwise indicated.

The invention claimed is:

1. A process for the recovery of a benzene rich liquid stream and a light ends vapor stream in a xylene isomerization process from a feedstock, the process comprising:
    passing a feedstock into a deheptanizer in which the feedstock is separated into a deheptanizer vapor phase and a deheptanizer liquid phase, the deheptanizer vapor phase containing hydrocarbons with seven carbon atoms or less, and the deheptanizer liquid phase containing hydrocarbons with eight carbon atoms or more;
    passing the deheptanizer vapor phase from the deheptanizer to a first separation zone;
    separating the deheptanizer vapor phase in the first separation zone into a first liquid phase and a first vapor phase;
    passing the first liquid phase from the first separation zone to a toluene recovery zone;
    passing the first vapor phase from the first separation zone to a compression zone in which the first vapor phase is compressed and partially condensed to provide a compressed and partially condensed vapor phase;
    passing the compressed and partially condensed vapor phase from the compression zone to a second separation zone;
    separating the compressed and partially condensed vapor phase into the benzene rich liquid stream and a second vapor phase in the second separation zone, the second vapor phase being a light ends vapor stream;
    recovering the light ends vapor stream;
    recovering the benzene rich liquid stream; and
    sending the benzene rich liquid stream to extraction.

2. The process of claim 1 further comprising passing a portion of the first liquid phase to the deheptanizer.

3. The process of claim 1 further comprising passing the benzene rich liquid stream to the extraction to recover a benzene stream.

4. The process of claim 1 further comprising passing the benzene rich liquid stream to storage.

5. The process of claim 1 further comprising compressing the deheptanizer vapor phase before the deheptanizer vapor stream enters the first separation zone.

6. The process of claim 5 wherein a temperature of the first separation zone is between approximately 32° C. to 149° C.

7. The process of claim 6 wherein a temperature of the second separation zone is between approximately 10° C. to 149° C.

8. The process of claim 1 wherein a temperature of the first separation zone is between approximately 10° C. to 149° C. and a temperature of the second separation zone is between approximately 10° C. to 149° C.

9. A process for the recovery of a benzene rich liquid stream and a light ends vapor stream in a xylene isomerization process from a feedstock, the process comprising:
    passing a feedstock into a distillation column in which the feedstock is separated into a distillation vapor and a distillation liquid, the distillation vapor containing mostly hydrocarbons with seven carbon atoms or less;
    condensing the distillation vapor;
    separating the distillation vapor into a first liquid phase and a first vapor phase;
    passing the first liquid phase to a toluene recovery zone;
    compressing the first vapor phase into a compressed vapor phase;
    separating the compressed vapor phase into the benzene rich liquid stream and a second vapor phase, the second vapor phase being a light ends vapor stream;
    recovering the light ends vapor stream;
    recovering the benzene rich liquid stream; and
    sending the benzene rich liquid stream to extraction.

10. The process of claim 9 wherein a temperature of the first liquid phase is between approximately 32° C. to 149° C.

11. The process of claim 10 wherein a temperature of the compressed vapor phase is between approximately 10° C. to 149° C.

12. The process of claim 9 further comprising passing a portion of the first liquid phase to the distillation column.

13. The process of claim 9 further comprising passing the benzene rich liquid stream to the extraction to recover a benzene stream.

14. The process of claim 9 further comprising passing the benzene rich liquid stream to storage.

15. A process for the recovery of a benzene rich liquid stream and a light ends vapor stream in a xylene isomerization process from a feedstock, the process comprising:
    passing a feedstock into a separation zone in which the feedstock is separated into a vapor stream and a liquid stream, the vapor stream containing mostly hydrocarbons with seven carbon atoms or less, the liquid stream comprising xylene;
    condensing the vapor stream;
    separating the condensed vapor stream into a first liquid phase and a first vapor phase;
    passing the first liquid phase to a toluene recovery zone;
    passing the first vapor phase to a compression zone;
    compressing the first vapor phase into a compressed vapor phase;
    separating the compressed vapor phase into the benzene rich liquid stream and a second vapor phase, the second vapor phase being a light ends vapor stream;
    recovering the light ends vapor stream; and
    recovering the benzene rich liquid stream; and
    sending the benzene rich liquid stream to extraction.

16. The process of claim 15 wherein a temperature of the first liquid phase is between approximately 32° C. to 149° C.

17. The process of claim 15 wherein a temperature of the compressed vapor phase is between approximately 10° C. to 149° C.

* * * * *